(12) United States Patent
Huang et al.

(10) Patent No.: US 11,506,651 B2
(45) Date of Patent: Nov. 22, 2022

(54) METHOD FOR EVALUATING MIXING EFFECT OF CO2 OIL-DISPLACING AND MIXING AGENT AND METHOD FOR SCREENING CO2 OIL-DISPLACING AND MIXING AGENT

(71) Applicant: Peking University, Beijing (CN)

(72) Inventors: Jianbin Huang, Beijing (CN); Cheng Ma, Beijing (CN); Kaerdun Liu, Beijing (CN); Yun Yan, Beijing (CN); Zhiyang Zhu, Beijing (CN)

(73) Assignee: Peking University, Beijing (CN)

( * ) Notice: Subject to any disclaimer, the term of this patent is extended or adjusted under 35 U.S.C. 154(b) by 183 days.

(21) Appl. No.: 16/918,468

(22) Filed: Jul. 1, 2020

(65) Prior Publication Data

US 2020/0333316 A1 Oct. 22, 2020

Related U.S. Application Data

(63) Continuation of application No. PCT/CN2019/072796, filed on Jan. 23, 2019.

(30) Foreign Application Priority Data

Jan. 23, 2018 (CN) .......................... 201810062778.3

(51) Int. Cl.
*G01N 33/28* (2006.01)
*E21B 49/00* (2006.01)
(Continued)

(52) U.S. Cl.
CPC ....... *G01N 33/2823* (2013.01); *E21B 49/003* (2013.01); *G01N 13/02* (2013.01); *G01N 33/2841* (2013.01); *E21B 43/164* (2013.01)

(58) Field of Classification Search
CPC . G01N 33/2823; G01N 33/2841; G01N 13/02
See application file for complete search history.

(56) References Cited

U.S. PATENT DOCUMENTS 4,627,273 A * 12/1986 Christiansen ...... G01N 33/2823
73/61.41
4,766,558 A * 8/1988 Luks ....................... E21B 43/16
700/265
(Continued)

FOREIGN PATENT DOCUMENTS

CN 206671293 U 11/2017
CN 107576778 A 1/2018

OTHER PUBLICATIONS

Yongmao, H. et al., "Laboratory Investigation of CO2 Flooding,"Society of Petroleum Engineers, 28th Annual SPE International Technical Conference and Exhibition, pp. 1-6, Aug. 2004.
(Continued)

*Primary Examiner* — John Fitzgerald
(74) *Attorney, Agent, or Firm* — Nixon Peabody LLP (57) ABSTRACT

Provided in the present invention a method for evaluating the mixing effect of a $CO_2$ oil-displacing and mixing agent, characterized in measuring the volume expansion of a $CO_2$-oil interface when pressure is gradually increased, drawing a mixed-phase percentage-pressure curve (δ-P curve), and evaluating the mixing effect of the $CO_2$ oil-displacing and mixing agent by means of comparing the characteristics of the δ-P curve. Further provided in the present invention is a method for initially screening a $CO_2$ oil-displacing and mixing agent.

15 Claims, 2 Drawing Sheets

(51) Int. Cl.
    *G01N 13/02*     (2006.01)
    *E21B 43/16*     (2006.01)

(56) References Cited

U.S. PATENT DOCUMENTS

| | | | | |
|---|---|---|---|---|
| 9,410,935 | B2 * | 8/2016 | Aquino Olivos .. | G01N 25/4873 |
| 9,851,339 | B2 * | 12/2017 | Hawthorne ........ | G01N 33/2823 |
| 2016/0047226 | A1 * | 2/2016 | Hawthorne ........ | G01N 33/2823 |
| | | | | 166/305.1 |

OTHER PUBLICATIONS

Yang, S. et al., "Molecular Optimization Design and Evaluation of Miscible Processing Aids Applied to CO2 Flooding," Xinjiang Petroleum Geology, vol. 26, No. 5, pp. 555-559, Oct. 2015.

\* cited by examiner

METHOD FOR EVALUATING MIXING EFFECT OF CO2 OIL-DISPLACING AND MIXING AGENT AND METHOD FOR SCREENING CO2 OIL-DISPLACING AND MIXING AGENT

REFERENCES TO RELATED APPLICATIONS

This application is a. U.S. bypass continuation of PCT/CN2019/072796 filed on Jan. 23, 2019. which claims the benefits of the Chinese patent application No. 201810062778.3, filed on Jan. 23, 2018 before the National Intellectual Property Administration, P. R. China, the contents of which are all incorporated herein by reference in their entireties.

TECHNICAL FIELD

The invention relates to a method for rapidly evaluating mixing effect (hereinafter also be referred as "miscibility aiding effect") of a $CO_2$ oil-displacing and mixing agent (hereinafter also be referred as "a mixing aid" for short), and in particular to a method for rapidly evaluating the miscibility aiding effect of a $CO_2$ oil-displacing and mixing agent via a volume expansion method, and belongs to the field of oilfield chemistry.

BACKGROUND

The $CO_2$ oil-displacing is a relatively novel way for oil-displacing and has been successfully applied in tertiary oil recovery in the United States. The $CO_2$ oil-displacing, especially the miscibility $CO_2$ oil-displacing, can greatly improve the oil-displacing ratio, thus the interest and research on $CO_2$ oil-displacing is rapidly advanced in the context of paying more attention to the full recovery of oil resources in the existing oil reservoir. However, there is no example of successful application of $CO_2$ oil-displacing in China up to now, and one reason therefor is significant differences in the compositions and properties of the oil reservoirs in China and those in US. In China, for the heavier oil phase composition and the higher viscosity, the miscibility pressure with $CO_2$ is larger. Such larger miscibility pressure not only brings higher operating cost, but also brings certain potential safety risks, and has serious impact on sweep efficiency and displacement efficiency, thus it is difficult to achieve the actual recovery ratio as ideally expected.

Therefore, it has become an important part for carrying forward the $CO_2$ oil-displacing to further reduce the miscibility pressure between the $CO_2$ and the crude oil. In the related studies, reducing the minimum miscibility pressure (MMP) via lowering the interfacial tension between crude oil and $CO_2$ by using a mixing aid is an important direction of current research. For a specific reservoir, to achieve a better $CO_2$ oil-displacing effect, it is desirable to screen the best one among a multitude of candidate mixing aids. In order to compare the miscibility aiding effects of different mixing aids during screening, it is often necessary to add a particular mixing aid and directly measure the corresponding minimum miscibility pressure. At present, measurement method for minimum miscibility pressure by slim tube test (Chinese oil industry standard SY/T 6573-2003) is a standard method for determining the miscibility pressure of simulating a $CO_2$ oil-displacing process in the art and has the most widely application, and the obtained minimum miscibility pressure value is also the most accurate. However, the method has a relative long operating cycle, typically longer than one month, and accordingly requires heavy experimental workload. Similarly, in order to determine the $CO_2$-oil interfacial tension, experimental methods such as bubble rise method, interfacial tension method and the like can also be used; however, these methods also have disadvantages such as long time consumption, large experimental workload and the like. In addition, other methods such as improved state equation methods, $CC_{MMP}$ predicting models, multi-contact characteristic lines predicting models and the like are also developed to estimate the minimum miscibility pressure (Non-Patent Document 1), however, all of these methods are still theoretical prediction methods based on experimental results. Therefore, in order to screen the mixing aids applicable to a specific actual oil reservoir system, a simple and rapid method for experimental evaluation on the miscibility aiding effect of the mixing aid is urgently needed in the art.

Non-Patent Document 1: Zhao Haifeng et al., Study of $CO_2$ miscible displacement mechanism and minimum miscibility pressure [J], China Petroleum and Chemical Standards and Quality, 2016, 36 (17): 95-98

SUMMARY OF THE INVENTION

In order to solve the above problem, through hard study with great concentration and numerous experiments, the inventors unexpectedly discovered that, by measuring the extent of oil volume expansion at different $CO_2$ pressure levels, the miscibility aiding effect of different mixing aids can be quantitatively compared simply and rapidly, and meanwhile, experimental evaluation on the miscibility aiding effect can be achieved relatively accurately, so that the appropriate mixing aid for a specific oil reservoir can be quickly screened, thus completed the present invention.

In a first aspect, the present invention provides a method of evaluating miscibility aiding effect of a $CO_2$ oil-displacing and mixing agent, characterized in that a volume expansion of $CO_2$-oil interface during gradual pressurization is measured and a mixed-phase percentage-pressure curve (hereinafter also be referred as "miscibility percentage-pressure curve" or "δ-P curve") is plotted, and the miscibility aiding effect of the $CO_2$ oil-displacing and mixing agent is evaluated by comparing characteristics of the δ-P curves.

In a preferred embodiment, the method comprises the steps of:

(1) Add a predetermined volume of the oil into a constant volume autoclave having an observation window and an inlet gas path, close the autoclave, place the autoclave in a constant-temperature water bath, observe from the observation window and record an initial liquid level $H_0$, and connect a $CO_2$ gas source and a pressure gauge to the inlet gas path;

(2) introduce high-pressure $CO_2$ loaded with a $CO_2$ oil-displacing and mixing agent to be tested into the autoclave until a pre-determined pressure level P is reached, turn off the inlet gas path, let stand until a gas-liquid equilibrium is reached, record pressure level P, observe from the observation window and record liquid level H;

(3) continuously introduce $CO_2$ to increase the pressure of the autoclave until another predetermined pressure level is reached, and record the corresponding pressure level and the liquid level according to the method of the step (2);

(4) repeat the step (3) until the liquid level rises to the ceiling of the autoclave tank, and record the corresponding pressure level $P_m$ and the ceiling height of the autoclave tank $H_m$;

(5) calculate the miscibility percentage δ corresponding to each pressure level according to the following Formula (1), and plot the δ-P curve:

$$\delta = \frac{H - H_0}{H_m - H_0} \times 100\% \quad \text{Formula (1)}$$

Subsequently, the autoclave is depressurized and cleaned;

(6) repeat the steps (1)-(5) by using different $CO_2$ oil-displacing and mixing agents to be tested to obtain δ-P curves corresponding to these $CO_2$ oil-displacing and mixing agents to be tested; and (7) compare the characteristics of the δ-P curves corresponding to these $CO_2$ oil-displacing and mixing agents to be tested, so as to evaluate the miscibility aiding effect of each $CO_2$ oil-displacing and mixing agent to be tested.

In a preferred embodiment, the oil is selected from one or more of kerosene, white oil and crude oil.

Preferably, in the step (1), the ratio of the initial liquid level $H_0$ to the ceiling height of the autoclave tank $H_m$ is 1:2 to 1:5, preferably 1:3; the temperature of the constant-temperature water bath is a constant temperature selected from a range of 40-80° C.

Preferably, in the step (2), the mass fraction of the mixing aid in the $CO_2$ gas ranges from 0.1% to 5%, preferably 1%; the pressurization is carried out by a single-cylinder plunger pump; the pre-determined pressure level is between 4-8 MPa, preferably 5 MPa; the gas-liquid equilibrium means that after the $CO_2$ inlet gas path is turned off, the pressure gauge reading changes by no more than 0.01 MPa and the liquid level changes by no more than 0.01 cm within 5 minutes.

Preferably, in the step (4), the $P_m$ is determined to be the minimum miscibility pressure.

Preferably, in the step (7), the characteristics are selected from one or more of the following factors: the corresponding liquid level H at a particular pressure level, the slope k of the curve at a particular pressure level, the corresponding $CO_2$ pressure level P when the liquid level reaches a particular height, and the $P_m$.

In another aspect, the present invention also provides a method of initially screening a mixing aid comprising: use the same amount of different mixing aids, evaluate the miscibility aiding effect by using the evaluation method of the present invention, and screen the desired mixing aid according to the characteristics of the miscibility percentage-pressure curve.

Compared with the prior art method, the method provided by the invention can conveniently and rapidly evaluate the miscibility aiding effect of the $CO_2$ oil-displacing and mixing agent, and the evaluation result is stable and reliable, the time and the workload required are remarkably reduced, and multiple experiments in large batches can be carried out simultaneously, so that the initially screening can be achieved during the research and development of the mixing aid, and the guiding quantitative evaluation of the corresponding mixing aid to be tested can be obtained. Therefore, the method of the present invention has significant advantages in leading frontier research of the field of $CO_2$ miscibility oil-displacing and subsequent industrial applications.

DETAILED DESCRIPTION

Although it is known to those skilled in the art that, during $CO_2$ oil-displacing, $CO_2$ gradually dissolves into the oil phase with gradual pressurization, resulting in volume expansion of the oil phase. However, the inventors have discovered for the first time that, since the mixing aid can increase the affinity between $CO_2$ and the oil, it is reflected macroscopically that the volume expansion of the oil phase will be further enlarged at the same pressure in the $CO_2$-oil system into which a mixing aid is added. Following this principle, for a mixing aid with better miscibility aiding effect, a miscibility percentage-pressure curve (δ-P curve) is further left-shifted, i.e., the same volume expansion effect is achieved at a lower pressure.

In some embodiments of the present disclosure, the miscibility percentage δ means that a percentage of the increase of the oil phase volume in the $CO_2$-oil system relative to the increase of the miscibility volume when a complete miscible phase forms between $CO_2$ and the oil phase. Accordingly, the miscibility percentage-pressure curve (δ-P curve) refers to the working curve resulting from changing the pressure level of the system and measuring the miscibility percentages at different pressure levels and plotting the miscibility percentages corresponding to the pressure levels, with other conditions remaining unchanged. Sometimes, a "volume change ratio-pressure curve" may also be used to indicate a δ-P curve, but it should not be considered that the miscibility percentage is limited to be represented only by the volume change ratio. In some embodiments, the δ-P curve is measured in a constant volume container, wherein the pressure is increased by introducing additional $CO_2$ into the container. In some embodiments, the δ-P curve can be measured in a variable volume container wherein the amount of $CO_2$ in the system remains unchanged, and the pressure is adjusted by changing the volume of the container. In fact, in the case that only different mixing aids are to be screened, any suitable method may be selected by those skilled in the art to obtain the δ-P curve, as long as the measurement conditions thereamong remain the same. In a preferred embodiment, in view of convenience for implementation and ease for controlling, the measurement is performed by using a constant volume container to obtain the δ-P curve.

The container used should be able to provide information on the oil phase volume. In some embodiments, in order to determine the oil phase volume when measuring, the container for measurement used is transparent. In some embodiments, the container for measurement has an observation window so that the oil phase volume can be determined by observing the height of the oil phase interface. In some embodiments, the container for measurement has a sensor that can acquire and output the oil phase volume.

Similarly, the container used should be able to provide the pressure information. In some embodiments, the pressure information is provided by the pressure gauge connected to the $CO_2$ gas path. In further embodiments, the container for measurement used has a sensor that can acquire and output the pressure information. In some embodiments, the container for measurement used is a constant volume autoclave with an observation window and an inlet gas path, wherein the height of the oil phase interface is observed from the observation window, and the pressure in the autoclave is determined via the inlet gas path.

In some embodiments of the present disclosure, further, in the constant volume autoclave, only one phase is present in the entire tank of the autoclave when the liquid level of the oil phase exactly rises to the ceiling of the autoclave tank, i.e., the miscible phase state is reached, so the corresponding pressure $P_m$ at this time is the minimum miscibility pressure.

In the context of the present invention, the "mixing aid" refers to any agent that is introduced into the oil-displacing system together with $CO_2$ carrier gas and plays a role in reducing the minimum miscibility pressure by reducing the interfacial tension between the oil phase and $CO_2$. Preferably, the mixing aid is a surfactant.

In a preferred embodiment, the step (2) may be carried out under stirring, preferably by using a magnetic stirrer, so as to achieve gas-liquid equilibrium more rapidly.

In the present invention, for the purpose of reducing the oil phase viscosity so as to facilitate stirring and thus accelerating the $CO_2$-oil phase to reach the gas-liquid equilibrium, while considering the need to simulate the actual formation reservoir temperature, the entire process is preferably conducted at a constant temperature selected from a range of 40-80° C. In some embodiments, the entire process is performed at a constant temperature that is the same as the formation temperature of the oil phase source. In some embodiments, the entire process is performed at a specific constant temperature that differs from the formation temperature of the oil phase source by no more than 20° C., preferably no more than 10° C., more preferably no more than 5° C. The formation temperature of the oil phase source refers to the temperature of the formation reservoir in which the oil phase is obtained. In some embodiments, the formation temperature of the oil phase source can be determined based on a randomly measured ten-point average of the temperature of the formation reservoir from which the oil phase is obtained.

Many variables are also present in the method of the present invention, which are also contemplated by the present invention. For example, it will be readily appreciated by those skilled in the art that the methods of the present invention may also be used to optimize the range of amounts of a particular mixing aid, so as to obtain an amount of the mixing aid which achieves a high balance between reagent cost and oil-displacing efficiency.

EXAMPLES

Next, the present invention is described in further details by way of example, but the invention is not limited to these examples.

The reagents used in the following examples are as follows:
Kerosene: Macklin, Model: K812242;
White oil: 5# white oil, provided by Research Institute of Petroleum Exploration and Development (RIPED) of China;
Crude oil: provided by a certain region of Changing Oilfield;
$CO_2$: 99.9% Pure High Pressure Gas Bottle, supplied by Beijing Haikeyuanchang Practical Gas Co. Ltd.;
Glyceryl trioctanoate: Chemically Pure, Macklin;
Glyceryl Trilaurate: Chemically Pure, Macklin;
Tween-80: Chemically pure, Sinopharm Chemical Reagent Co. Ltd.

Constant volume autoclave: self-manufactured, having an observation window and a gas path, and using a single-cylinder plunger pump to introduce the gas.

Example 1

20.00 ml of kerosene was added into a constant volume autoclave, then a stirring magnetic bar was added and the constant volume autoclave was closed, placed in a constant-temperature water bath with water temperature of 40° C., and the initial liquid level ($H_0$) was recorded; a $CO_2$ inlet gas path was connected to introduce high-pressure $CO_2$ loaded with 1 wt % glyceryl trioctanoate as the mixing aid into the autoclave until the pressure reached 5 MPa, and then the $CO_2$ inlet gas path was turned off, and let stand for more than half an hour to reach equilibrium until the reading of the pressure gauge changed no more than 0.01 MPa and the liquid level changed by no more than 0.01 cm within 5 minutes. Then, the corresponding pressure level (P) and liquid level (H) were recorded at that time. Afterwards, $CO_2$ was further introduced to increase the pressure of the system to reach a specified pressure level, and then the corresponding pressure level and liquid level were recorded. This process was then repeated until the liquid level rises to the ceiling of the autoclave tank, at which the pressure $P_m$ and the ceiling height of the autoclave tank $H_m$ were recorded.

The volume change ratio corresponding to each pressure level was calculated according to the following formula. Then the δ-P curve was plotted.

$$\delta = \frac{H - H_0}{H_m - H_0} \times 100\%$$

Under the same conditions, glycerol trilaurate and Tween-80 were used as the mixing aids and evaluated for the miscibility aiding effect thereof, and the results were shown as Example 2 and Example 3, respectively; in addition, the same system without using any mixing aid was also measured and the results were shown as Comparative Example 1.

Figure 1:
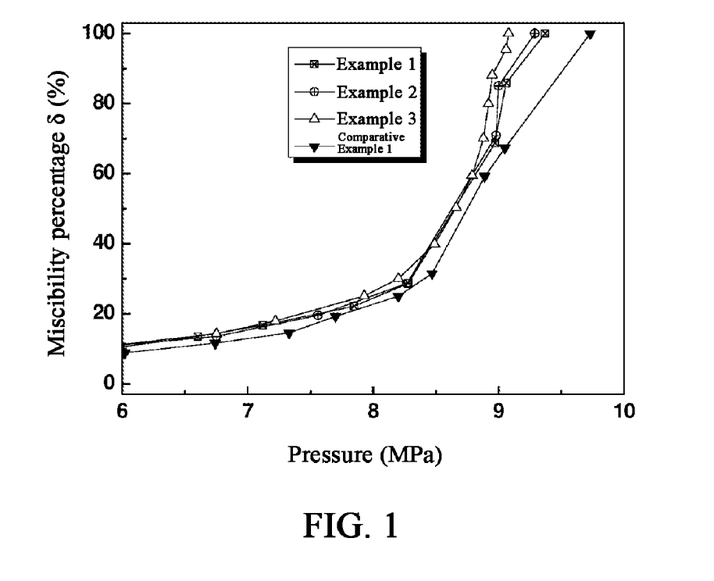
FIG. 1 shows the δ-P curves in a $CO_2$-kerosene system with glyceryl trioctanoate, glyceryl trilaurate or Tween-80 as the mixing aids respectively by the method of Examples 1-3 and Comparative Example 1.

FIG. 1 shows the δ-P curves of Examples 1-3 and Comparative Example 1. As can be easily seen from FIG. 1, each of Examples 1-3 has lower $P_m$ values as compared to Comparative Example 1, and each of the entire curve shows a trend of being left-shifted; on the other hand, by comparing the δ-P curve characteristics of Examples 1-3, the corresponding miscibility aiding effects of these mixing aids can be easily compared and screened.

The same test method as in Example 2 was used except changing the amount of glycerol trilaurate as 0.5 wt % and 2 wt %, and the results were shown as Example 4 and Example 5, respectively.

Figure 2:
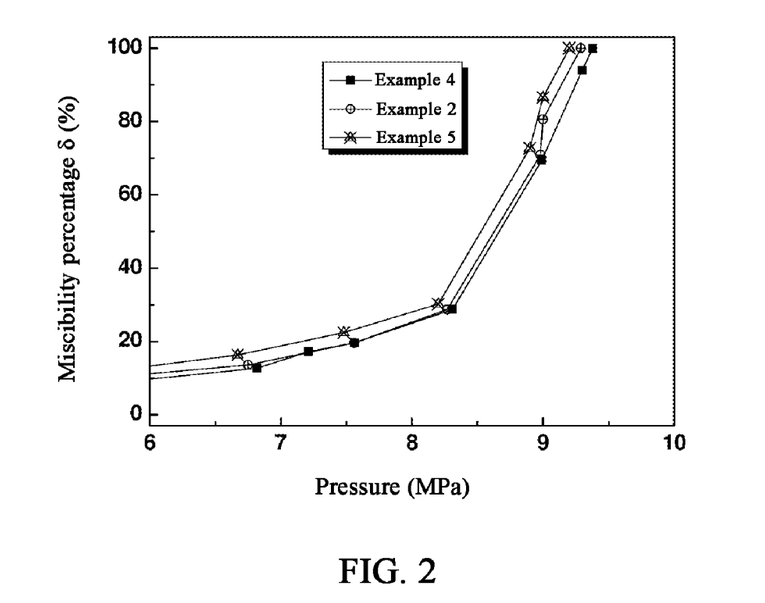
FIG. 2 shows the δ-P curves obtained in a $CO_2$-kerosene system with different concentrations of glyceryl trilaurate as the mixing aid by the method of Examples 2, 4 and 5.

FIG. 2 shows the δ-P curves of Example 2, Example 4 and Example 5. As can be seen from FIG. 2, as the concentration of glycerol trilaurate increases, the $P_m$ value decreases, and the entire curve is left-shifted.

Using the same test method as in Example 1 except using 1 wt % glycerol trilaurate as the mixing aid and the temperature of the constant temperature water bath was adjusted to 50° C. and 60° C., and the results were shown as Example 6 and Example 7, respectively.

Figure 3:
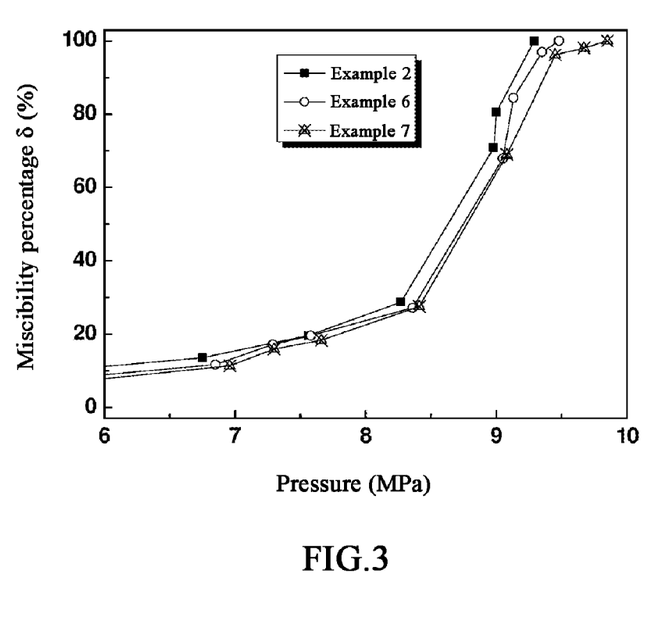
FIG. 3 shows the δ-P curves obtained in a $CO_2$-kerosene system with glyceryl trilaurate as the mixing aid at different temperatures by the method of Examples 2, 6 and 7.

FIG. 3 shows the δ-P curves of Example 2, Example 6 and Example 7. As can be seen from FIG. 3, with the temperature increases, the $P_m$ value also increases, and the entire curve shows a trend of being right-shifted.

Further, the experiment of Example 8 was conducted under the same conditions as Example 1 except using 1 wt % of glycerol trilaurate as the mixing aid and replacing kerosene with white oil. Further, the experiment of Example 9 was conducted under the same conditions as Example 1 except using 1 wt % of glycerol trilaurate as the mixing aid and replacing kerosene with crude oil.

Figure 4:
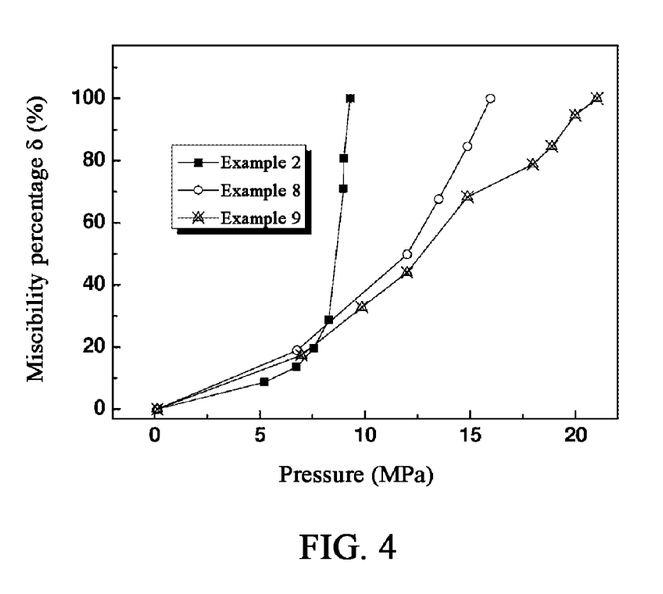
FIG. 4 shows the δ-P curves obtained in a $CO_2$-kerosene system, a $CO_2$-white oil system or in a $CO_2$-crude oil system respectively with glyceryl trilaurate as the mixing aid by the method of Examples 2, 8 and 9.

FIG. 4 shows the δ-P curves of Example 2, Example 8 and Example 9. As can be seen from FIG. 4, in kerosene, the mixing aid of Example 2 rapidly achieved a very high percentage of miscibility at lower concentrations, thus kerosene has a significantly better miscibility aiding effect compared to the white oil system of Example 8 and the crude oil system of Example 9.

In addition, for Example 9, the minimum miscibility pressure of crude oil obtained by Non-patent Document 2 using the interfacial tension method is 20.04 MPa; accordingly, the minimum miscibility pressure obtained in Example 9 is 21.03 MPa. Both results are substantially consistent with each other, and thus it can be seen that the method of the present invention can obtain the minimum miscibility pressure value of the $CO_2$-oil phase system in a relatively accurate way.

Non-Patent Document 2: Yang Siyu et al. The optimization and evaluation of mixing aid molecules for $CO_2$ oil-displacing [J], Xinjiang Petroleum Geology, 2015, 36 (5): 555-559.

The pressure-liquid level data of Examples 1-9 and Comparative Example 1 described above are shown in Table 1 below.

TABLE 1

Pressure-Liquid Level Data

| Pressure Level P/ MPa | Liquid Level H/ cm | Miscibility Percentage δ % |
|---|---|---|
| Example 1 | | |
| 0.13 | 2.89 | 0.00 |
| 5.23 | 3.45 | 8.35 |
| 6.00 | 3.60 | 10.58 |
| 6.60 | 3.80 | 13.56 |
| 7.12 | 4.01 | 16.69 |
| 7.85 | 4.38 | 22.21 |
| 8.28 | 4.82 | 28.76 |
| 8.97 | 7.50 | 68.70 |
| 9.06 | 8.65 | 85.84 |
| 9.37 | 9.60 | 100.00 |
| Example 2 | | |
| 0.13 | 2.90 | 0.00 |
| 5.22 | 3.48 | 8.66 |
| 6.75 | 3.81 | 13.58 |
| 7.56 | 4.21 | 19.55 |
| 8.27 | 4.82 | 28.66 |
| 8.98 | 7.65 | 70.90 |
| 9.00 | 8.60 | 85.07 |
| 9.29 | 9.60 | 100.00 |
| Example 3 | | |
| 0.13 | 2.91 | 0.00 |
| 4.67 | 3.41 | 7.47 |
| 5.77 | 3.60 | 10.31 |
| 6.75 | 3.87 | 14.35 |
| 7.22 | 4.11 | 17.94 |
| 7.93 | 4.59 | 25.11 |
| 8.20 | 4.92 | 30.04 |
| 8.49 | 5.58 | 39.91 |
| 8.66 | 6.28 | 50.37 |
| 8.79 | 6.89 | 59.49 |
| 8.88 | 7.60 | 70.10 |
| 8.92 | 8.26 | 79.97 |
| 8.95 | 8.81 | 88.19 |
| 9.06 | 9.30 | 95.52 |
| 9.08 | 9.60 | 100.00 |
| Example 4 | | |
| 0.13 | 2.90 | 0.00 |
| 5.31 | 3.38 | 7.16 |
| 6.82 | 3.75 | 12.69 |
| 7.21 | 4.05 | 17.16 |
| 7.56 | 4.21 | 19.55 |
| 8.31 | 4.82 | 28.66 |
| 8.99 | 7.55 | 69.40 |
| 9.30 | 9.20 | 94.03 |
| 9.38 | 9.60 | 100.00 |
| Example 5 | | |
| 0.13 | 2.90 | 0.00 |
| 5.21 | 3.55 | 9.70 |
| 6.67 | 3.99 | 16.27 |
| 7.48 | 4.40 | 22.39 |
| 8.20 | 4.92 | 30.15 |
| 8.90 | 7.77 | 72.69 |
| 9.00 | 8.70 | 86.57 |
| 9.20 | 9.60 | 100.00 |
| Example 6 | | |
| 0.14 | 2.90 | 0.00 |
| 5.32 | 3.35 | 6.72 |
| 6.85 | 3.68 | 11.64 |
| 7.29 | 4.05 | 17.16 |
| 7.58 | 4.21 | 19.55 |
| 8.36 | 4.72 | 27.16 |
| 9.05 | 7.45 | 67.91 |
| 9.13 | 8.56 | 84.48 |
| 9.35 | 9.40 | 97.01 |
| 9.48 | 9.60 | 100.00 |
| Example 7 | | |
| 0.15 | 3.00 | 0.00 |
| 5.43 | 3.38 | 5.76 |
| 6.96 | 3.75 | 11.36 |
| 7.30 | 4.05 | 15.91 |
| 7.66 | 4.21 | 18.33 |
| 8.41 | 4.82 | 27.58 |
| 9.08 | 7.55 | 68.94 |
| 9.45 | 9.35 | 96.21 |
| 9.67 | 9.47 | 98.03 |
| 9.85 | 9.60 | 100.00 |
| Example 8 | | |
| 0.13 | 7.01 | 0.00 |
| 6.77 | 7.50 | 18.92 |
| 12.00 | 8.30 | 49.81 |
| 13.50 | 8.76 | 67.57 |
| 14.87 | 9.20 | 84.56 |
| 15.96 | 9.60 | 100.00 |
| Example 9 | | |
| 0.13 | 7.01 | 0.00 |
| 6.98 | 7.46 | 17.37 |
| 9.85 | 7.86 | 32.82 |
| 12.00 | 8.15 | 44.02 |
| 14.87 | 8.78 | 68.34 |
| 17.98 | 9.05 | 78.76 |
| 18.88 | 9.20 | 84.56 |
| 19.98 | 9.46 | 94.59 |
| 21.03 | 9.60 | 100.00 |
| Comparative Example 1 | | |
| 0.13 | 2.81 | 0.00 |
| 4.81 | 3.19 | 5.60 |

TABLE 1-continued

Pressure-Liquid Level Data

| Pressure Level P/ MPa | Liquid Level H/ cm | Miscibility Percentage $\delta$ % |
|---|---|---|
| 5.25 | 3.35 | 7.95 |
| 6.02 | 3.41 | 8.84 |
| 6.74 | 3.60 | 11.63 |
| 7.33 | 3.80 | 14.58 |
| 7.70 | 4.12 | 19.29 |
| 8.20 | 4.51 | 25.04 |
| 8.47 | 4.95 | 31.52 |
| 8.89 | 6.83 | 59.20 |
| 9.05 | 7.38 | 67.30 |
| 9.73 | 9.60 | 100.00 |

Embodiments of the present invention are described in details above, but the present invention is not limited to the specific details of the above-described embodiments. Various simple variations of the technical solution of the present invention can be made within the scope of the technical concept of the present invention, and these simple variations are within the scope of the present invention.

It should be noted that each of the specific technical features described in the above embodiments can be combined in any suitable manner as long as no contradiction is caused. In order to avoid unnecessary repetition, the various possible combination manners are no longer described in the present invention.

In addition, the various different embodiments of the present invention may also be carried out in any combination as long as it does not contravene the idea of the present invention, which should also be regarded as the disclosure of the present invention.

What is claimed is:

1. A method for evaluating miscibility aiding effect of a $CO_2$ oil-displacing and mixing agent, the method comprising:

measuring a volume expansion of $CO_2$-oil interface during pressurization;

plotting a miscibility percentage-pressure curves ($\delta$-P curves); and evaluating the miscibility aiding effect of the $CO_2$ oil-displacing and mixing agent by comparing characteristics of the $\delta$-P curves, wherein the characteristics are selected from one or more of the following factors: the slope k of the curve at a particular pressure level, and the $P_m$.

2. The method according to claim 1, wherein the oil is selected from one or more of kerosene, white oil and crude oil.

3. A method of initially screening a $CO_2$ oil-displacing and mixing agent comprising: using the same amount of different $CO_2$ oil-displacing and mixing agents, evaluating the miscibility aiding effect by the evaluation method according to claim 1, and screening the desired $CO_2$ oil-displacing and mixing agent according to the characteristics of the curves $\delta$-P curves, wherein the characteristics are selected from one or more of the following factors: the slope k of the curve at a particular pressure level, and th $P_m$.

4. The method according to claim 1, the method comprising the steps of:

(1) adding a predetermined volume of the oil into a constant volume autoclave having an observation window and an inlet gas path, closing the autoclave, placing the autoclave in a constant-temperature water bath, observing from the observation window and recording an initial liquid level $H_0$, and connecting a $CO_2$ gas source and a pressure gauge to the inlet gas path;

(2) introducing high-pressure $CO_2$ loaded with the $CO_2$ oil-displacing and mixing agent to be tested into the autoclave until a pre-determined pressure level P is reached, turning off the inlet gas path, letting, stand until a gas-liquid equilibrium is reached, recording pressure level P, observing from the observation window and recording liquid level H;

(3) continuously introducing $CO_2$ to increase the pressure of the autoclave until another predetermined pressure level is reached, and recording the corresponding pressure level and the liquid level according to the method of the step (2);

(4) repeating the step (3) until the liquid level rises to the ceiling of the autoclave tank, and recording the corresponding pressure level Pm and the ceiling height of the autoclave tank $H_m$;

(5) calculating the miscibility percentage $\delta$ corresponding to each pressure level according to the following Formula (1), and plot the $\delta$-P curve:

$$\delta = \frac{H - H_0}{H_m - H_0} \times 100\% \qquad \text{Formula (1)}$$

subsequently, the autoclave is depressurized and cleaned;

(6) repeating the steps (1)-(5) by using different $CO_2$ oil-displacing and mixing agents to be tested to obtain $\delta$-P curves corresponding to these $CO_2$ oil-displacing and mixing agents to he tested; and (7) comparing the characteristics of the $\delta$-P curves corresponding to these $CO_2$ oil-displacing and mixing agents to be tested, so as to evaluate the miscibility aiding effect of each $CO_2$ oil-displacing and mixing agent to be tested.

5. The method according to claim 4, wherein in the step (1), the ratio of the initial liquid level $H_0$ to the ceiling height of the autoclave tank $H_m$ is 1:2 to 1:5, the temperature of the constant-temperature water bath is a constant temperature selecting from a range of 40-80° C.

6. The method according to claim 4, wherein in the step (2), the mass fraction of the $CO_2$ oil-displacing and mixing agent in the $CO_2$ gas ranges from 0.1% to 5%; the pressurization is carried out by a single-cylinder plunger pump; the pre-determined pressure level is between 4-8 MPa; the gas-liquid equilibrium refers to that after the $CO_2$ inlet gas path is turned off, the pressure gauge reading changes by no more than 0.01 MPa and the liquid level changes by no more than 0.01 cm within 5 minutes.

7. The method according to claim 4, wherein in the step (4), the Pm is determined to be the minimum miscibility pressure.

8. The method according to claim 3, wherein in the step (1), the ratio of the initial liquid level $H_0$ to the ceiling height of the autoclave tank $H_m$ is 1:3.

9. The method according to claim 3, wherein in the step (2), the mass fraction of the $CO_2$ oil-displacing and mixing agent in the $CO_2$ gas is 1%; the pressurization is carried out by a single-cylinder plunger pump; the pre-determined pressure level is 5 MPa; the gas-liquid equilibrium refers to that after the $CO_2$ inlet gas path is turned off, the pressure gauge reading changes by no more than 0.01 MPa and the liquid level changes by no more than 0.01 cm within 5 minutes.

10. A method for evaluating miscibility aiding effect of a $CO_2$ oil-displacing and mixing agent, the method comprising:
   measuring a volume expansion of $CO_2$-oil interface during pressurization;
   plotting a miscibility percentage-pressure curves (δ-P curves); and
   evaluating the miscibility aiding effect of the $CO_2$ oil-displacing and mixing agent by comparing characteristics of the δ-P curves,
   wherein in the characteristics are selected from two or more of the following factors: the corresponding liquid level H at a particular pressure level, the slope k of the curve at a particular pressure level, the correspondin $CO_2$ pressure level P when the liquid level reaches a particular height, and the $P_m$.

11. The method according to claim 10, wherein the oil is selected from one or more of kerosene, white oil and crude oil.

12. The method according to claim 10, the method comprising the steps of:
   (1) adding a predetermined volume of the oil into a constant volume autoclave having an observation window and an inlet gas path, closing the autoclave, placing the autoclave in a constant-temperature water bath, observing from the observation window and recording an initial liquid level $H_0$, and connecting a $CO_2$ gas source and a pressure gauge to the inlet gas path;
   (2) introducing high-pressure $CO_2$ loaded with the $CO_2$ oil-displacing and mixing agent to be tested into the autoclave until a pre-determined pressure level P is reached, turning off the inlet gas path, letting stand until a gas-liquid equilibrium is reached, recording pressure level P, observing front the observation window and recording liquid level H;
   (3) continuously introducing $CO_2$ to increase the pressure of the autoclave until another predetermined pressure level is reached, and recording the corresponding pressure level and the liquid level according to the method of the step (2);
   (4) repeating the step (3) until the liquid level rises to the ceiling of the autoclave tank, and recording the corresponding pressure level $P_m$ and the ceiling height of the autoclave tank $H_m$;
   (5) calculating the miscibility percentage δ corresponding to each pressure level according to the following Formula (1), and plot the δ-P curve:

$$\delta = \frac{H - H_0}{H_m - H_0} \times 100\% \qquad \text{Formula (1)}$$

subsequently, the autoclave is depressurized and cleaned;
   (6) repeating the steps (1)-(5) by ausing different $CO_2$ oil-displacing and mixing agents to be tested to obtain δ-P curves corresponding to these $CO_2$ oil-displacing and mixing agents to be tested; and
   (7) comparing the characteristics of the δ-P curves corresponding to these $CO_2$ oil-displacing and mixing agents to be tested, so as to evaluate the miscibility aiding effect of each $CO_2$ oil-displacing and mixing agent to be tested.

13. The method according to claim. 12, wherein in the step (1), the ratio of the initial liquid level Ho to the ceiling height of the autoclave tank $H_m$ is 1:2 to 1:5; the temperature of the constant-temperature water bath is a constant temperature selecting from a range of 40-80° C.

14. The method according to claim 12, wherein in the step (2), the mass fraction of the CO2 oil-displacing and mixing agent in the $CO_2$ gas ranges from 0.1% to 5%; the pressurization is carried out by a single-cylinder plunger pump; the pre-determined pressure level is between 4-8 MPa; the gas-liquid equilibrium refers to that after the $CO_2$ inlet gas path is turned off, the pressure gauge reading changes by no more than 0.01 MPa and the liquid level changes by no more than 0.01 cm within 5 minutes.

15. The method according to claim 12, wherein the step (4), the $P_m$ is determined to be the minimum miscibility pressure.

* * * * *

UNITED STATES PATENT AND TRADEMARK OFFICE
CERTIFICATE OF CORRECTION

PATENT NO. : 11,506,651 B2
APPLICATION NO. : 16/918468
DATED : November 22, 2022
INVENTOR(S) : Huang et al.

It is certified that error appears in the above-identified patent and that said Letters Patent is hereby corrected as shown below:

In the Claims

At Column 9, Line 59 (Claim 3, Line 7), please delete "$\delta$-P curves" and insert --($\delta$-P curves)-- therefor.

At Column 9, Line 61 (Claim 3, Line 9), please delete "and th $P_m$" and insert --and the $P_m$-- therefor.

At Column 10, Line 8 (Claim 4, Line 14), please delete "turning off the inlet gas path, letting, stand" and insert --turning off the inlet gas path, letting stand-- therefor.

At Column 10, Line 20 (Claim 4, Line 25), please delete "pressure level Pm" and insert --pressure level $P_m$-- therefor.

At Column 10, Line 34 (Claim 4, Line 34), please delete "mixing agents to he tested" and insert --mixing agents to be tested-- therefor.

At Column 10, Line 55 (Claim 7, Line 2), please delete "the Pm is determined" and insert --the $P_m$ is determined-- therefor.

At Column 10, Line 57 (Claim 8, Line 1), please delete "according to claim 3" and insert --according to claim 4-- therefor.

At Column 10, Line 60 (Claim 9, Line 1), please delete "according to claim 3" and insert --according to claim 4-- therefor.

At Column 11, Line 14 (Claim 10, Line 14), please delete "the correspondin $CO_2$" and insert --the corresponding $CO_2$-- therefor.

At Column 11, Line 35 (Claim 12, Line 16), please delete "observing front the observation window" and insert --observing from the observation window-- therefor.

Signed and Sealed this
Twenty-first Day of March, 2023

Katherine Kelly Vidal
*Director of the United States Patent and Trademark Office*

At Column 12, Line 14 (Claim 12, Line 36), please delete "by ausing different" and insert --by using different-- therefor.

At Column 12, Line 23 (Claim 13, Line 1), please delete "according to claim. 12" and insert --according to claim 12-- therefor.

At Column 12, Line 24 (Claim 13, Line 2), please delete "the initial liquid level Ho" and insert --the initial liquid level $H_0$-- therefor.

At Column 12, Line 29 (Claim 14, Line 2), please delete "the mass fraction of the CO2" and insert --the mass fraction of the $CO_2$-- therefor.

At Column 12, Line 37 (Claim 15, Line 1), please delete "wherein the step (4)" and insert --wherein in the step (4)-- therefor.